(12) United States Patent
Kadota (10) Patent No.: US 8,181,519 B2
(45) Date of Patent: *May 22, 2012

(54) RESISTANCE-BASED MUSCULAR FORCE EVALUATION AND TRAINING UTILIZING ELASTICITY FOLLOWING ANGULAR CHANGE OF FIRST AND SECOND JOINTS

(75) Inventor: Kenji Kadota, Gunma (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 1079 days.

This patent is subject to a terminal disclaimer.

(21) Appl. No.: 12/039,321

(22) Filed: Feb. 28, 2008

(65) Prior Publication Data

US 2008/0207409 A1   Aug. 28, 2008

(30) Foreign Application Priority Data

Feb. 28, 2007  (JP) .................................. 2007-48517

(51) Int. Cl.
*A61B 5/22* (2006.01)
(52) U.S. Cl. .................................................... 73/379.01
(58) Field of Classification Search ............... 73/379.01, 73/379.02
See application file for complete search history.

(56) References Cited

U.S. PATENT DOCUMENTS

| 7,748,271 | B2* | 7/2010 | Kadota | 73/379.01 |
| 2008/0202232 | A1* | 8/2008 | Kadota | 73/379.01 |
| 2010/0050765 | A1* | 3/2010 | Kadota et al. | 73/379.01 |

FOREIGN PATENT DOCUMENTS

| JP | 10-94524 | 4/1998 |
| JP | 2000-210272 | 8/2000 |
| JP | 2003-220102 | 8/2003 |
| JP | 2006-43871 | 2/2006 |
| JP | 2006-340746 | 12/2006 |

OTHER PUBLICATIONS

T. Fujikawa, et al. "Coordinate Activities of a Group of Monoarticular Muscle and a Group of Bi-articular Muscles in Upper Limbs, Acting in Antagonism to One Another, and Analysis of Control Functions thereof by a Mechanical Model", Biomechanisms 13, The Society of Biomechanisms, pp. 181-191, 1996.

* cited by examiner

*Primary Examiner* — Jewel V Thompson
(74) *Attorney, Agent, or Firm* — Rabin & Berdo, PC

(57) ABSTRACT

In an apparatus for resistance-based muscular force evaluation and training, elasticity at the distal end of a robot arm is made to follow changes caused in the force exerted by the muscles of praxis as a result of changes in angle at the first and second joints. Even when the trainee changes his or her position, he or she may be indicated of and may positively comprehend the direction in which he or she is to exert the force. The robot arm have its distal end secured to the distal end of the link mechanism has elasticity variable with directions. The elasticity is varied to follow changes caused in the force exerted on the distal end of the link mechanism by a set of antagonistic mono-articular muscles and a set of antagonistic bi-articular muscles, as a result of changes in angle at the first and second joints.

7 Claims, 9 Drawing Sheets

RESISTANCE-BASED MUSCULAR FORCE EVALUATION AND TRAINING UTILIZING ELASTICITY FOLLOWING ANGULAR CHANGE OF FIRST AND SECOND JOINTS

BACKGROUND OF THE INVENTION

1. Field of the Invention

The present invention relates to an apparatus, a method and a system for resistance-based muscular force evaluation and training.

2. Description of the Background Art

A resistance-based muscular force training system, such as a bi-articular arm device, exploiting a bi-articular link mechanism has been proposed in Japanese patent laid-open publication No. 2000-210272, for instance. There has also been disclosed, for a system or an apparatus for evaluating or training the muscular force of a user, using a robot arm fastened to his or her limbs, the technique for indicating the direction of the force to be exerted by the user, based on elasticity of the distal end of the robot arm, which is made hard or soft depending on the direction of force application.

In the aforementioned conventional systems for resistance-based muscular force evaluation and training, the modulus of elasticity in a specified direction is constant regardless of the positions of the four limbs. However, the force actually generated at the distal ends of the four limbs of the human body may be varied appreciably in dependent upon the position or orientation of the limbs. Thus, if the trainee changes his or her position so that the force which he or she can exert at the distal ends of his or her limbs becomes greater or smaller, then he or she may feel the elasticity changing hard or soft accordingly, thus possibly causing cases where the elasticity felt hard or soft distinguishably is indefinite. In such a case, the trainee is unable to comprehend the direction in which to exert his or her force.

SUMMARY OF THE INVENTION

It is therefore an object of the present invention to provide an apparatus for resistance-based muscular force evaluation and training, which can properly indicate, even when a trainee changes his or her position, the direction in which he or she is to exert his or her force to the trainee to help the trainee properly comprehend the direction for force application. It is also an object of the invention to provide such a method and a system.

In an apparatus for resistance-based muscular force evaluation and training in accordance with the present invention, the elasticity at the distal end of a robot arm is made to follow a change in force exerted by the muscles of praxis at the distal end of a link mechanism, the change being brought about with an angular change of the first and second joints.

In accordance with the present invention, a system for resistance-based evaluation and training of a bi-articular link mechanism of the muscular force of a trainee comprises a robot arm which comprises: a first link having opposite ends respectively connectable to a first joint and a second joint; and a second link having one end connectable to the second joint and another end corresponding to a distal end of the bi-articular link mechanism. The bi-articular link mechanism includes a set of antagonistic mono-articular muscles about the first joint and another set of antagonistic mono-articular muscles about the second joint, both sets of muscles producing an exercise movement in a plane including the first and second joints and the distal end of the link mechanism, and a set of antagonistic bi-articular muscles astride the first and second joints. The robot arm has a distal end secured to the distal end of the link mechanism, and the distal end of the robot arm exhibits elasticity variable with direction. The elasticity is variable to follow a change associated with an angular change of the first and second joints in a force exerted at the distal end of the link mechanism by the set of antagonistic mono-articular muscles and the set of antagonistic bi-articular muscles. The variable elasticity is used to indicate the trainee of a direction in which he or she is to exert the force at the distal end of the link mechanism.

Also according to the present invention, the system for resistance-based evaluation and training may further comprise a saddle for the trainee to sit on, a fastener for securing the robot arm to the upper or lower limb of the trainee, a controller for controlling the torque at a first joint or the axis of a second joint of the robot arm, and an angular sensor for sensing joint angles of the robot arm. The robot arm is adjustable to the length of an upper limb or a lower limb of the trainee. The controller controls the stiffness at the distal end of the robot arm.

Further according to the present invention, in the system for resistance-based evaluation and training, the stiffness may be expressed in a form of ellipse in a plane having two axes corresponding to the torque at the first joint and the torque at the second joint. The ellipse has a constant eigenvalue in each of a first direction in which the trainee is to exert the force and a second direction substantially perpendicular to the first direction.

Still further according to the present invention, an apparatus for resistance-based evaluation and training of a bi-articular link mechanism of the muscular force of a trainee comprises a saddle for a trainee to sit on; a robot arm adjustable to a length of an upper limb or a lower limb of the trainee and having a distal end exhibiting elasticity variable with direction; a fastener for securing the robot arm to the upper limb or the lower limb of the trainee; a controller for controlling torques at first and second joints on the robot arm; and an angular sensor for sensing the joint angle of the robot arm. The controller exercises control to cause the elasticity to vary to follow a change in position of the upper or lower limb of the trainee to use the variable elasticity to indicate the trainee of a direction in which the trainee is to exert a force to measure his or her muscular force.

Also according to the present invention, in a method for resistance-based evaluation and training of a muscular force of a bi-articular link mechanism of a trainee, the bi-articular link mechanism includes a set of antagonistic mono-articular muscles about a first joint and another set of antagonistic mono-articular muscles about a second joint, both sets of muscles producing an exercise movement in a plane including the first and second joints and a distal end of the link mechanism, and a set of antagonistic bi-articular muscles astride said first and second joints. The method comprises: preparing a robot arm including a first link having opposite ends respectively connectable to the first joint and second joint, and a second link having one end connectable to the second joint and another end corresponding to the distal end of the link mechanism; causing elasticity at a distal end of the robot arm, when secured to the distal end of the link mechanism, to follow a change associated with an angular change of the first and second joints of a force exerted at the distal end of the link mechanism by the set of antagonistic mono-articular muscles and the set of antagonistic bi-articular muscles; and using the variable elasticity to indicate a direction in which the trainee is to exert the force at the distal end of the link mechanism.

With the resistance-based muscular force evaluation and training system, according to the present invention, the modulus of elasticity at the distal end of the robot arm is varied to follow changes caused in the force exerted on the distal end of the link mechanism by a set of antagonistic mono-articular muscles and a set of antagonistic bi-articular muscles, as a result of changes in angle at the first and second joints. Even when the trainee changes his or her position, he or she may be indicated as to the direction in which he or she is to exert the force and may positively comprehend such a direction.

BRIEF DESCRIPTION OF THE DRAWINGS

The objects and features of the present invention will become more apparent from consideration of the following detailed description taken in conjunction with the accompanying drawings in which.

DESCRIPTION OF THE PREFERRED EMBODIMENTS

With reference to the accompanying drawings, preferred embodiments of the present invention will now be described in detail. First, with reference to FIG. 3, the reference numeral 20 denotes a user, or trainee, in the present illustrative embodiment. The user 20 performs evaluation and training of his or her muscular force using the resistance-based muscular force evaluation and training system. Initially, by way of giving the background information on the resistance-based muscular force evaluation and training system, the bi-articular link mechanism of the limbs of a human body will be described insofar as such a description is necessary for understanding the present invention.

Figure 6:
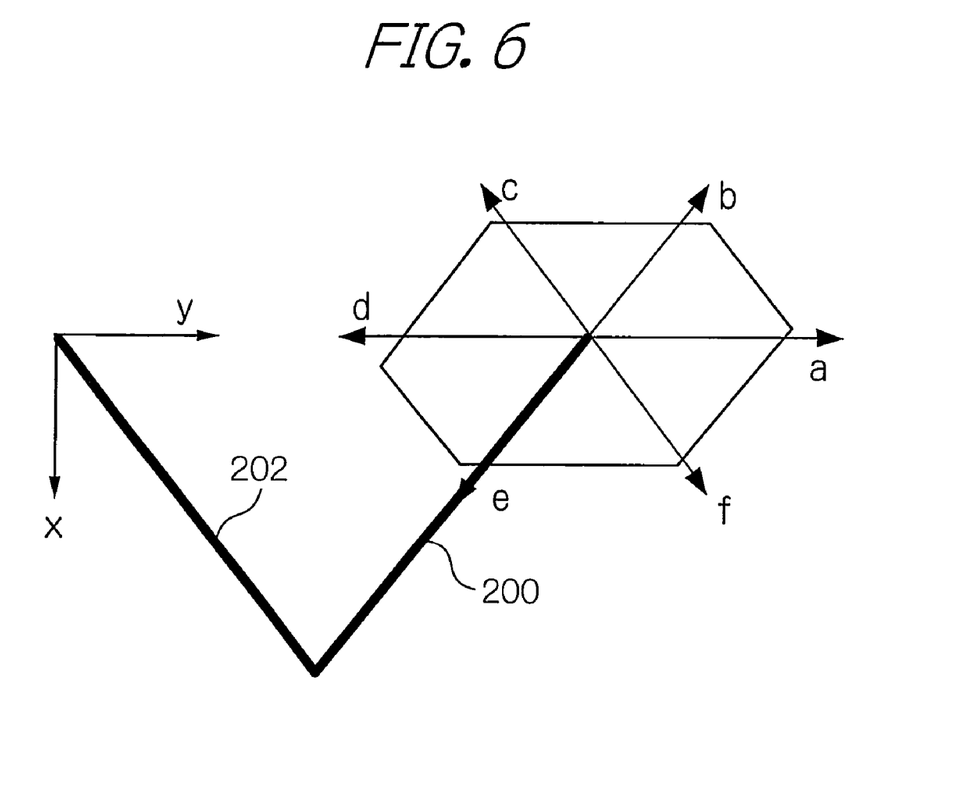
FIGS. 6 and 7 are graphs showing the output distribution of the force at the distal end of the link mechanism, and a diagram showing the output distribution of the torques at the joint axles, respectively, according to the preferred embodiment.
Figure 7:
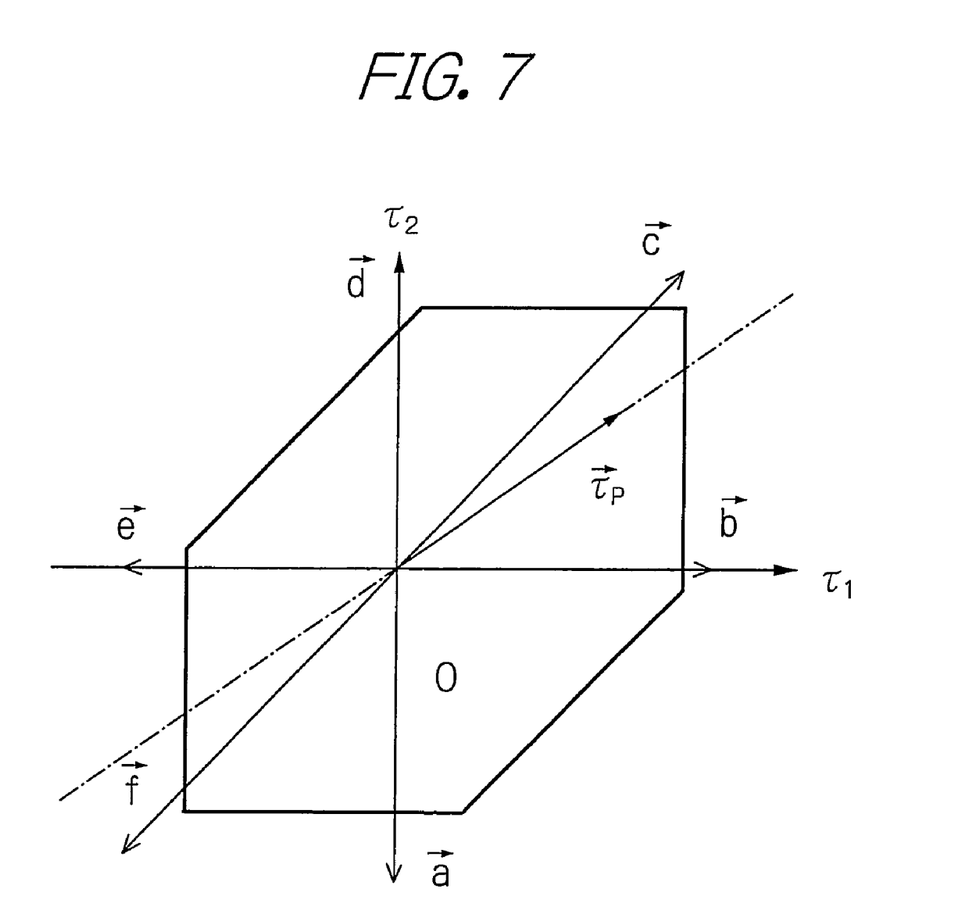

As known, bi-articular muscles are present in the limbs, that is, four limbs, of the human body, and act in coordinate with the mono-articular muscles, operating on a sole joint, to control an output at the distal end thereof. This output may be represented by a hexagonal diagram of the characteristics of output distribution, as shown in FIGS. 6 and 7, which is disclosed for example in T. Fujikawa et al., "Coordinate Activities of a Group of Mono-articular Muscles and a Group of Bi-articular Muscles in Upper Limbs Acting in Antagonism to One Another, and Analysis of Control Functions thereof by a Mechanical Model", Biomechanisms 13, The Society of Biomechanisms, pp. 181-191, 1996. There is also known a method for evaluating the force of function-based muscles of praxis, in accordance with a hexagonal diagram of the characteristics of output distribution, as disclosed for example in Japanese '272 publication mentioned above.

The output characteristics at the distal ends of the four limbs, disclosed in both of these prior art documents, will now be described insofar as such a description is necessary for understanding the present invention.

Figure 3:
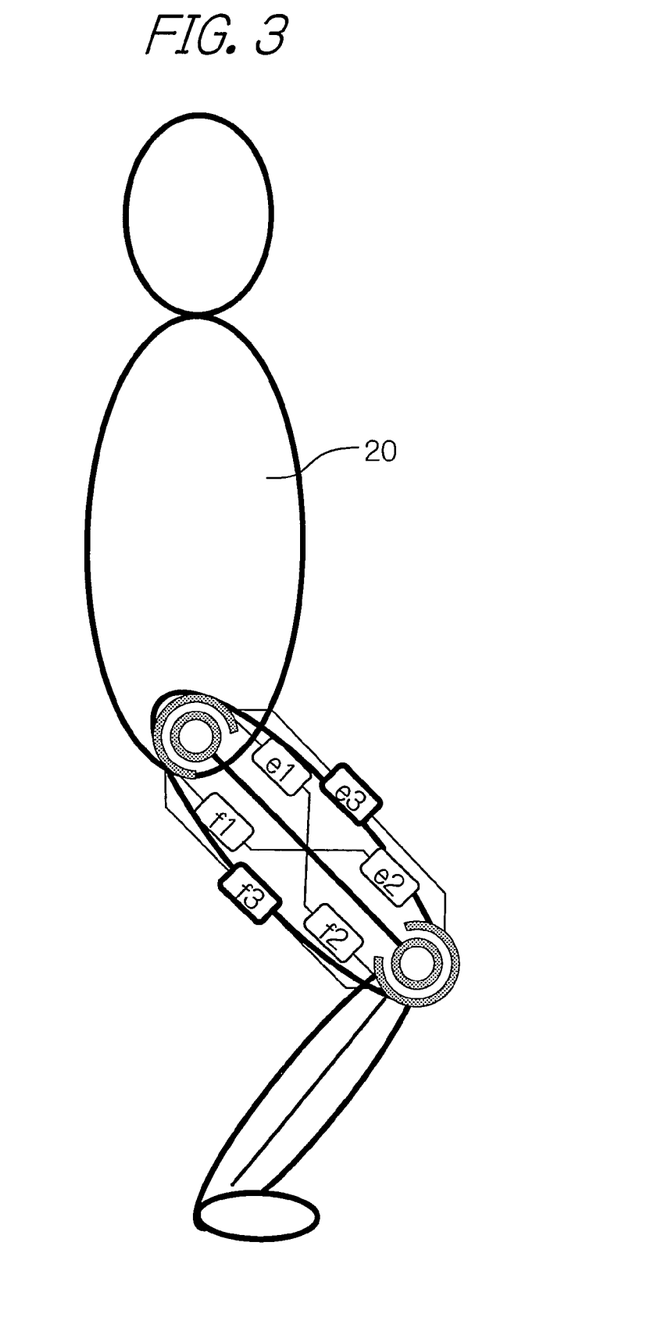
FIG. 3 schematically shows groups of muscles of a user's limb in a preferred embodiment of the present invention.

In each of the upper and lower limbs of a human body, the muscles that act on first and second joints, in exercise movements in a two-dimensional plane including a first joint, a second joint and a distal end of the pertinent system, i.e. the link system, or mechanism, of a bi-articular link mechanism of the trainee, or subject person, may be represented by three pairs of muscles, i.e. six muscles, as shown in FIG. 3. If the functions of the muscles are taken in to account, these muscles are an antagonistic mono-articular muscle pair (f1, e1) around the first joint, an antagonistic mono-articular muscle pair (f2, e2) around the second joint, and an antagonistic bi-articular muscle pair (f3, e3), lying astride the first and second joints. The muscles are termed function-based muscles of praxis. The muscles shown by way of example in FIG. 3 are a group of muscles acting on a hip and a knee joint of the lower limb of the user 20.

The mono-articular muscle refers to a muscle acting only on a sole joint. The mono-articular muscle of the upper limb may be exemplified by the anterior or posterior part of a deltoid of a shoulder joint, a brachia muscle of an elbow joint and the caput lateralis (outer head) of the triceps of the upper arm. The mono-articular muscle of the lower limb may be exemplified by musculus gluteus maximus, waist joint, caput breve (short head) of biceps of thigh and vastus lateralis of the knee joint. Specifically, the bi-articular muscles of the upper limb may be exemplified by the biceps of the upper arm and the caput longum (long head) of the triceps of the upper arm, while that of the lower limb may be exemplified by ham strings or the straight muscle of thigh.

Figure 4:
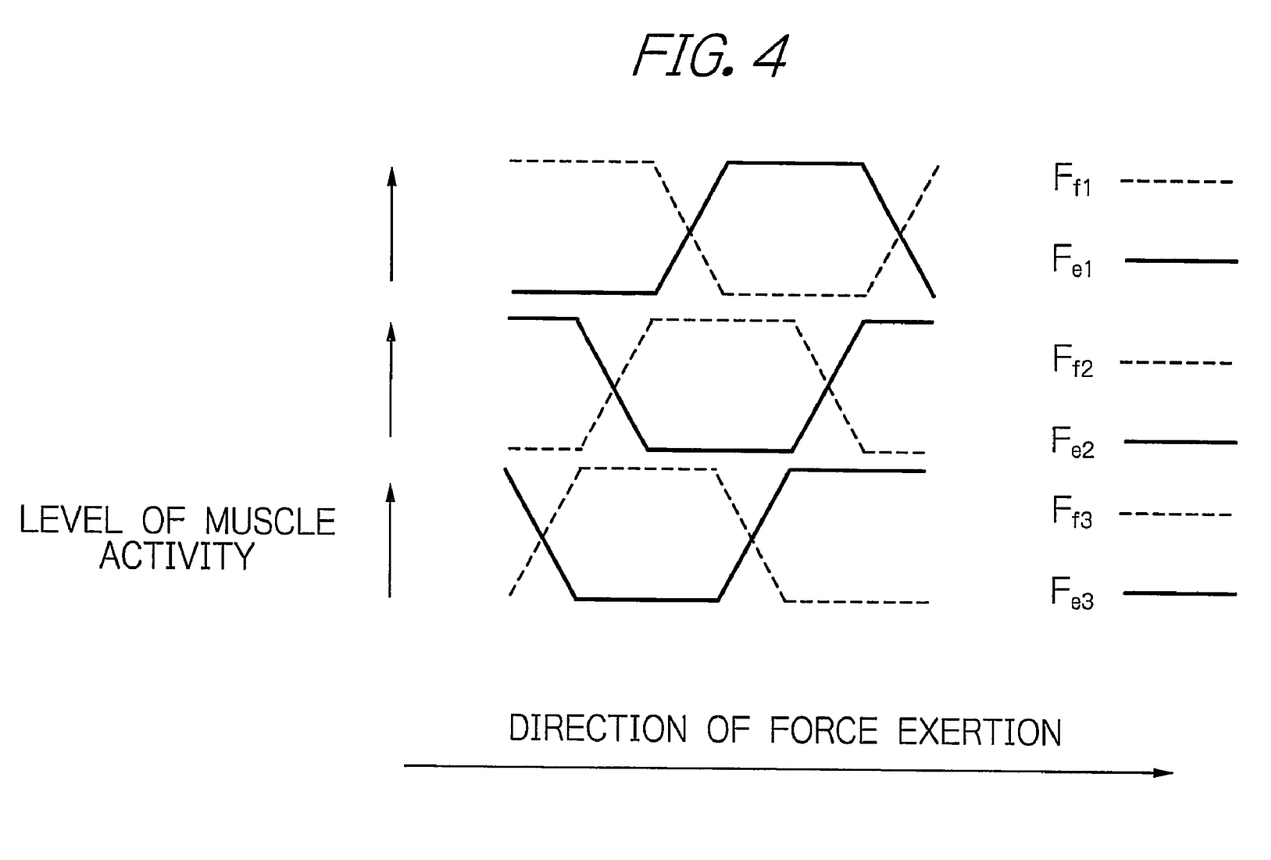
FIG. 4 schematically shows in the form of graph the degree or pattern of activities of the muscles of the user's limb in the preferred embodiment.

An output exhibited at the distal end of a system of the bi-articular link of the upper or lower limb of the human body, that is, at the joint of the wrist part of a hand for the upper limb and at the ankle joint for the lower limb, and the direction of the output, are controlled by the coordinate activities of the function-based muscles of praxis, namely the aforementioned three pairs of muscles, i.e. six muscles. If the force is exerted with the maximum effort in respective directions at the distal end of the link system, then the function-based muscles of praxis, namely the aforementioned three pairs of muscles, are alternately contracted, depending on the directions of force application, as shown in FIG. 4. In this figure, F denotes the magnitude of the force of the joint muscles indicated by the suffixes.

The force generated at the distal end of the limb, due to the contractile force, exhibited by the three paired function-based muscles of praxis, at the distal end of the limb, has its directions as illustrated in FIG. 4. More specifically, a hexagonal diagram of characteristics of maximum output distribution is exhibited as forces combined under the coordinate control in accordance with the alternate pattern shown in FIG. 4.

It is characteristic that the sides of the hexagon of the maximum output distribution characteristics are parallel to the first and second links, and a straight line interconnecting the first joint and the distal end of the link system. Hence, the hexagonal shape differs with the positions of the limbs. Even though the contractile forces of the muscles remain constant, so that the torque generated in each joint is not changed, the force generated at the distal end of the limb of the human body is changed, in direction and magnitude, by the axial torques at the joints, depending on the positions of the upper or lower limb.

Figure 1:
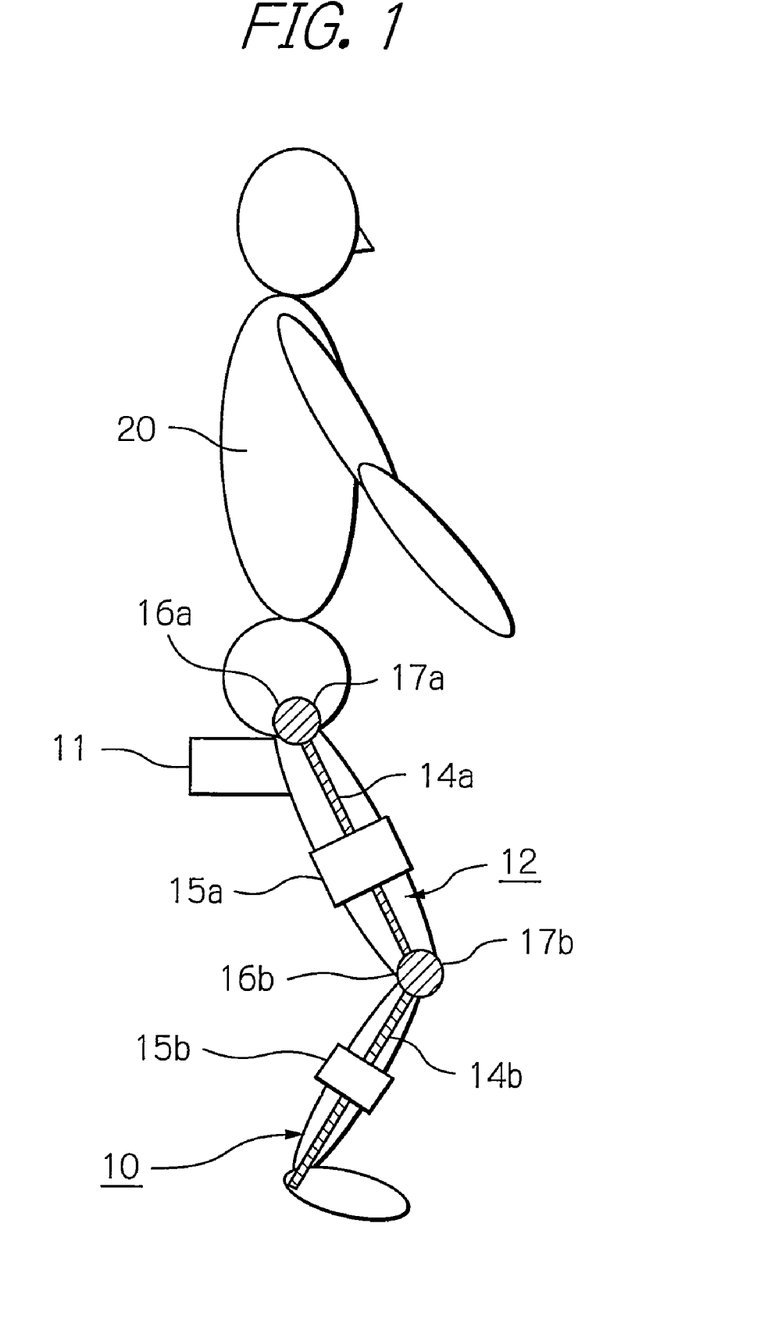
FIG. 1 is a side elevation schematically showing a use environment of a resistance training apparatus in accordance with the present invention.
Figure 2:
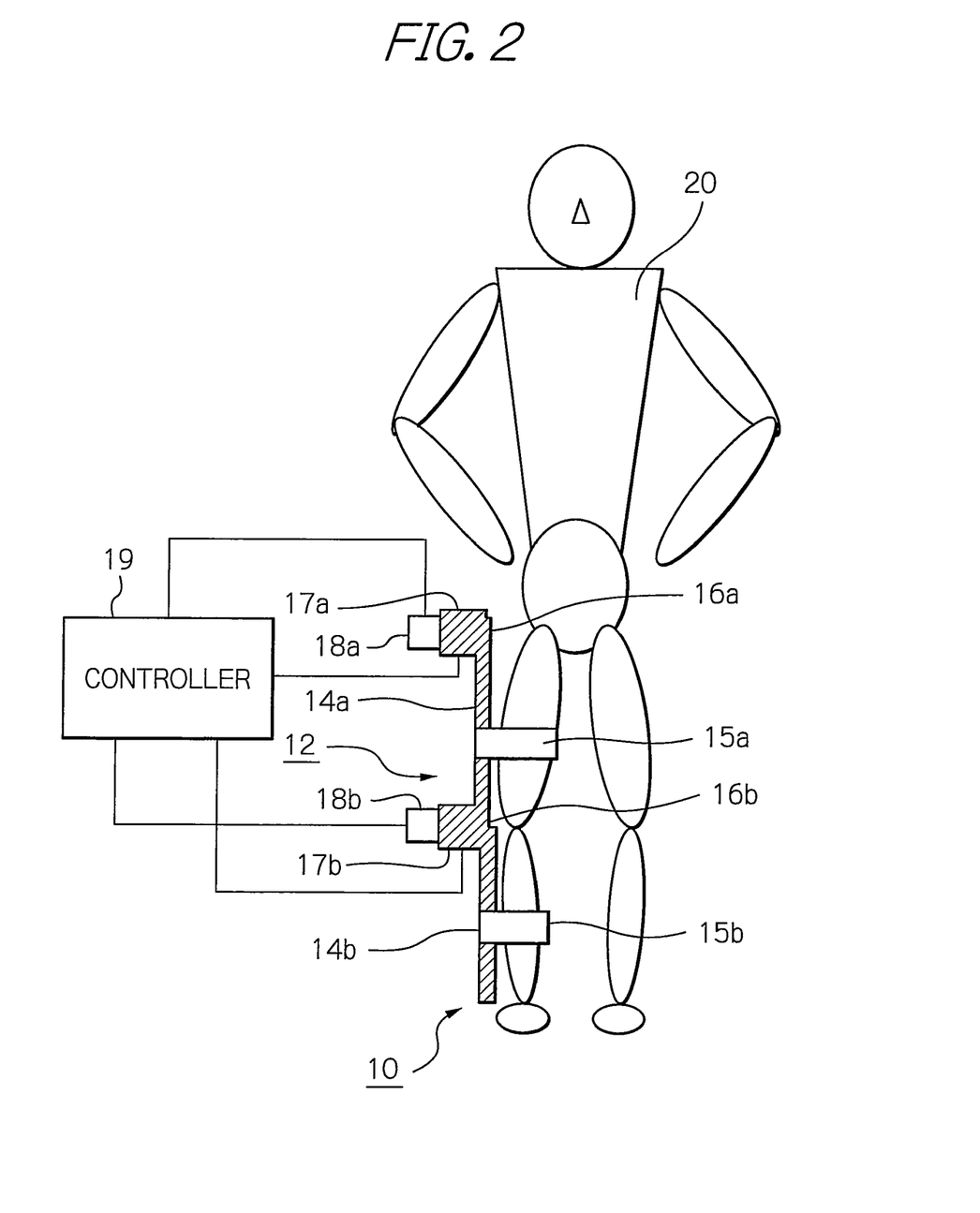
FIG. 2 is a front view schematically showing the use environment of the resistance training apparatus shown in FIG. 1.

The constitution of the resistance-based muscular force evaluation and training apparatus 10, used in the system for muscular force evaluation and training of the present illustrative embodiment, will now be described. FIGS. 1 and 2 schematically show the constitution of the muscular force evaluation and training apparatus 10 in accordance with the embodiment in the form of side and front views, respectively.

The resistance-based muscular force evaluation and training apparatus 10 of the instant embodiment provides for most effective resistance-based muscular force evaluation and training, as the aforementioned output characteristics of the limb of the human body are taken into account. Referring to FIG. 1, the resistance-based muscular force evaluation and training apparatus 10 is made up of a saddle 11, on which sits a user 20, a robot arm 12, a controller 19 for controlling the robot arm 12, and an operational console, not shown, for allowing a user, or trainee, 20 to input his or her intention of having his or her muscular force evaluated and/or trained. The robot arm 12 is attached for extending along the limb of the user 20. Although the lower limb is taken here for description, the system may apply for the upper limb as well.

The robot arm 12 is made up of two links, that is, a first link 14a for a thigh and a second link 14b for a lower leg, and hence has its degree of freedom equal two. The first link 14a and the second link 14b are each provided with a slide mechanism for adjusting the link length. For resistance-based muscular force evaluation, the first and second links are adjusted so as to be almost or substantially equal in length to the thigh and the foot of the user 20, respectively, and are fastened to the thigh and the leg using a first fastener 15a and a second fastener 15b, respectively. The first link 14a and the second link 14b may sometimes be referred collectively to as a link 14. The first fastener 15a and the second fastener 15b may also sometimes be referred collectively to as a fastener 15.

The robot arm 12 is worn by the user 20 when he or she is seated on the saddle 11. At this time, a first joint axle 16a of the robot arm 12 is brought into register with the hip joint of the user 20, and a second joint axle 16b of the robot arm 12 is brought into register with axis of his or her knee joint.

To the first joint axle 16a and the second joint axle 16b, connected are a first servo motor 17a and a second servo motor 17b, respectively. There is also provided absolute type encoders, e.g. angular sensors 18a and 18b, for sensing the joint angles. The first joint axle 16a and the second joint axle 16b may sometimes be referred to collectively as a joint axle 16. The first servo motor 17a and the second servo motor 17b may also sometimes be referred to collectively as a servo motor 17. The servo motor 17 operates as a driving source for the joint and generates a torque for rotating the joint axle. The torque generated by the servo motor 17 is controlled by the aforementioned controller 19. The torques generated by the joint axles of the robot arm 12 may be recorded by a recorder, not shown, connected to the controller 19.

To the controller 19 are connected a display unit, which may be a cathode-ray tube (CRT), a liquid crystal display or electro-luminescence display device, not shown, and an output device, such as a printer. The output device is for use in displaying or printing a hexagonal diagram plotting an output distribution prepared, as will be described later on, or informing the user 20 of the directions in which the force is to be applied, for example.

Figure 8:
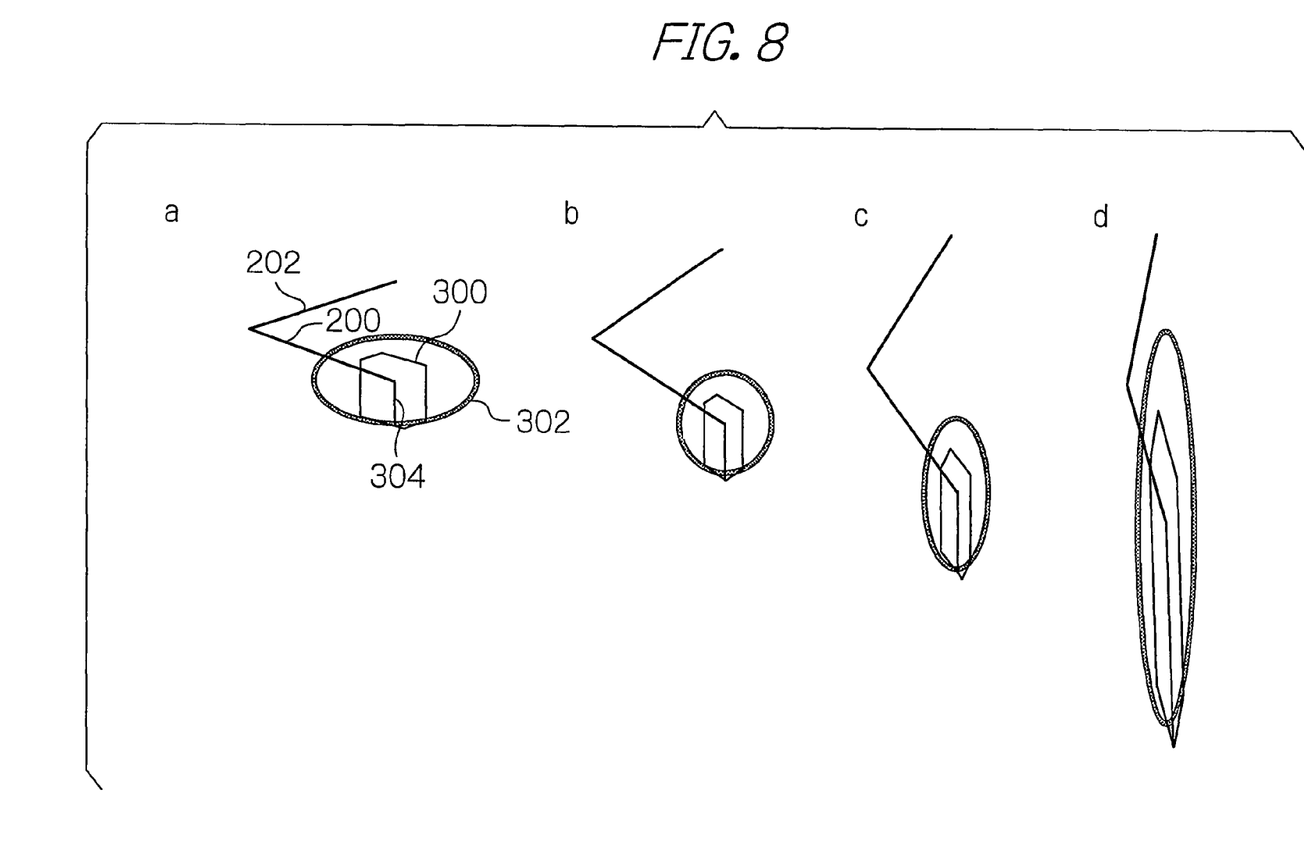
FIG. 8 schematically shows changes in a stiffness ellipse in the preferred embodiment.

The operation of the above-described muscular force evaluating and training apparatus 10 will now be described in detail. FIGS. 6 and 7 show the distribution of the force output at the distal end of the link system, as contrasted to the output of the torques at the joint axles, in the illustrative embodiment. FIG. 8 shows changes in stiffness ellipse in the embodiment. More specifically, FIG. 6 shows the output distribution of the torque at the distal end of the link system, and FIG. 7 shows the output distribution of the torques at the joint axles. FIG. 8, portions (a) to (d) show changes in stiffness ellipse corresponding to the state of the second joint extending.

The output distribution of the force, exerted at the distal end of the link system, more specifically, at the joint of the wrist part of the hand for the upper limb or at the ankle joint for the lower limb, is varied with the joint angle of the link system. Thus, with the present embodiment, an output distribution diagram of the torques at the joint axles which is shown in FIG. 7 is taken up for scrutiny in which the axial torques at the first joint ($\tau 1$) and the second joint ($\tau 2$) which could be generated at the respective joints simultaneously are plotted on the abscissa and the ordinate, respectively.

According to the theory of the function-based muscles of praxis, the output distribution of the torques at the joint axles is hexagonally shaped, like the distribution of the force output at the distal end of the link system, such as shown in FIG. 6. The output distribution of the torques at the joint axles, shown in FIG. 7, is correlated with the output distribution of the force at the distal end of the link system shown in FIG. 6.

The correlation between the two hexagons, shown in FIGS. 6 and 7, will now be described. FIG. 6 represents output distribution characteristics in the Japanese '272 publication stated earlier. In the hexagon shown in FIG. 6, the two sides parallel to a second rod, that is, the second link 200, are not changed in moment about the second joint. Hence, these sides are equivalent to straight lines which are parallel to the $\tau 1$ axis, where $\tau 2$=constant, in the diagram of the output distribution of the torques at the joint axles. In a similar manner, also in the hexagon shown, the two sides parallel to a straight line interconnecting the first joint and the distal end of the link system are not changed in moment about the first joint. Hence, in the diagram of output distribution of the torques at the joint axles, the above two sides are equivalent to straight lines parallel to the $\tau 2$ axis, where $\tau 1$=constant.

Among the sides of the hexagon, shown in FIG. 6, the two sides parallel to the first rod, that is, to the first link 202, will now be taken up for scrutiny. As regards the changes in force from one of the ends to the opposite ends of these sides, the direction of the changes in force is of the first link 202, so that these sides may be thought of as affording the same changes in torque at the first and second joints. Hence, these two sides are equivalent to straight lines parallel to a line for $\tau 1$=$\tau 2$.

If it is possible to measure the output distribution of the torques at the joint axles, such as shown as a diagram in FIG. 7, it is also possible to obtain the diagram for the output distribution at the distal end of the link for optional joint angles.

In order to evaluate the force of the individual function-based muscles of praxis, this force may be evaluated by specifying the cross-sectional area, less the fat part, of the antagonistic bi-articular muscle pair, as taught in the Japanese '272 publication.

In order to obtain a diagram for output distribution of the torques at the joint axles, the user 20 exerts the force with the maximum effort in various directions, as the robot arm 12 is attached for extending along the lower limb of the user 20. In this state, the force exerted by the user 20 with maximum effort is recorded as the torque at the joint axle. In this case, the user 20 is to exert the force as he or she is indicated, e.g. visually, of the direction for force application. Since the robot arm 12 generates the force of reaction for the user, as the torque at the joint axis is controlled to prevent the joint angle from being changed, the torque at the joint axis when the joint angle is not changed is recorded as the torque at the joint axis as exerted by the user 20.

The values of the so recorded torques at the joint axles are plotted on the τ1-τ2 coordinate plane, shown in FIG. 8, as the torque values that can be generated simultaneously by the two joint axles. A hexagon of the smallest size is drawn which contains the set of all plots, with its two sides parallel to the τ1-axis, with its other two sides parallel to the τ2-axis and with its remaining two sides parallel to a line of τ2=τ1, and used as a diagram of output distribution of the torques at the joint axles. Hexagons formed using the resistance-based muscular force evaluation and training apparatus 10 before the user 20 proceeds to training and after he or she has finished the training may be displayed on the same viewing screen, as shown in FIG. 8, to help the user 20 comprehend the changes in his or her muscular force before and after the training.

The user 20 may also perform training using the resistance-based muscular force evaluation and training apparatus 10. In performing the training, the user 20 operates the operational console for the apparatus 10, to input a training menu or schedule. The training menu is input as the user inputs the output direction in which lies the distal end of the limb the user wants to train, and the magnitude of the training load, based on the hexagonal shape of distribution characteristics of the maximum output, shown for example in FIG. 5.

Figure 5:
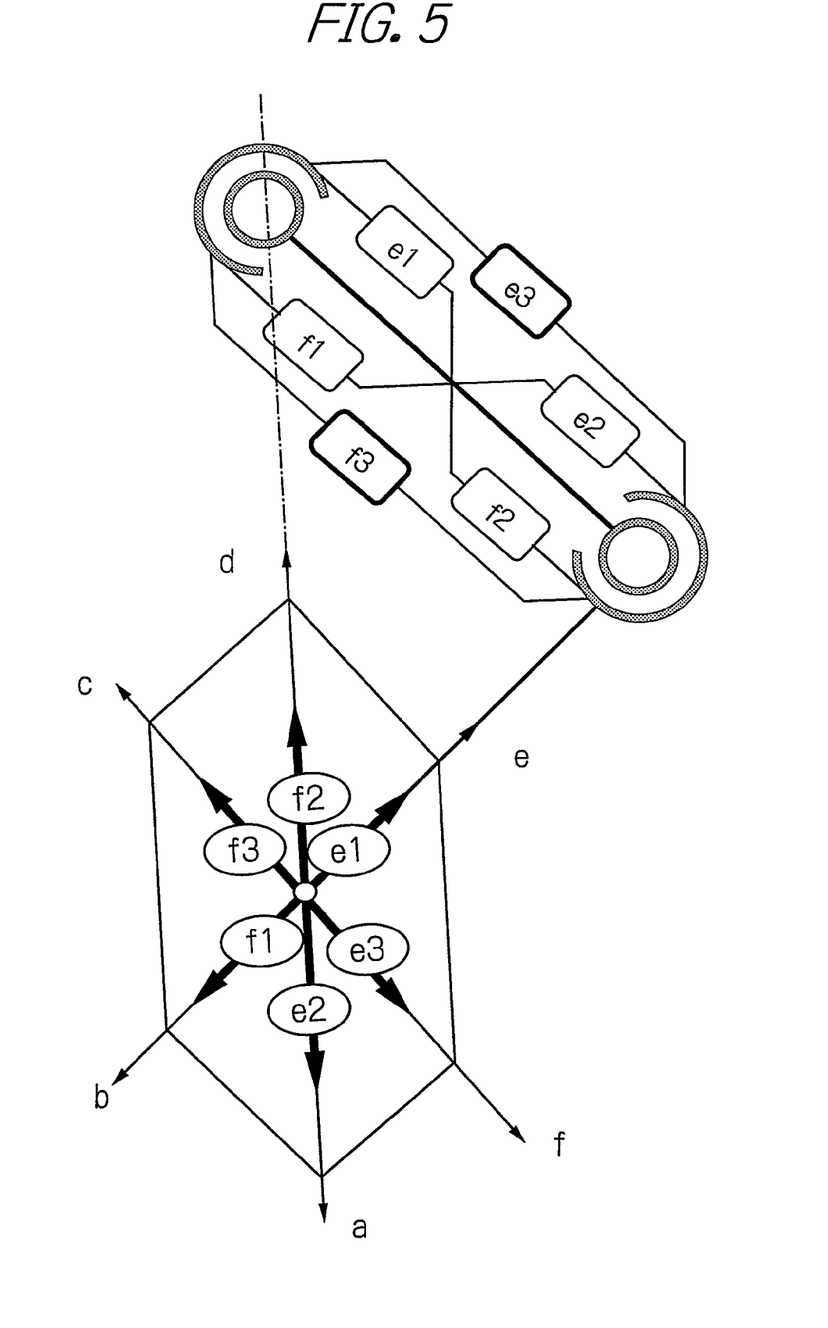
FIG. 5 schematically shows characteristics of the output distribution of the muscles of the user's limb in the preferred embodiment.

For example, it is supposed that the user 20 intends to increase the jump distance of a standing broad jump, and hence to augment the output at the distal end in a direction b in lower one 30 of the hexagons shown in FIG. 5. The user 20 then selects the direction b as the output direction for training, while inputting the magnitude of the training load. It is seen from the alternating pattern of the three pairs of muscles, shown in FIG. 4, that the muscles that are in operation when the user 20 exerts the force in the direction b are f1 (group of hip joint mono-articular flexors), e2 (group of knee joint mono-articular flexors) and f3 (group of bi-articular flexors for thigh).

For augmenting the output at the distal end, in the direction b, it is sufficient to train the group of three muscles, that is, f1, e2 and f3. Hence, in the resistance-based muscular force evaluation and training apparatus 10, the torques generated by the first servo motor 17a and the second servo motor 17b, associated with the hip and knee joints, respectively, when the above group of three muscles is in operation, are increased in the opposite directions, either progressively or stepwise, up to the magnitude of the training load as input by the user 20. The user 20 then exerts the force to oppose to the torques generated by the apparatus 10 to maintain the state of the preset muscle output, thereby training his or her muscular force.

Since the resistance-based muscular force evaluation and training apparatus 10 exerts a constant torque as a load to the user 20, he or she may perform the isometric training provided that he or she makes an endeavor not to change the position of the distal end of his or her limb (ankle in the above example). Moreover, since the load applied to the muscle is not changed even if the position of the user 20 is changed during training, the user may perform the isotonic training.

When the user 20 performs the evaluation and training of his/her muscular force, the resistance-based muscular force evaluation and training apparatus 10 indicates, for the user 20, the direction in which he or she is to exert his or her force, based on stiffness characteristics at the distal end of the robot arm 12 attached to his or her upper or lower limb. More specifically, the modulus of elasticity in a certain direction at the distal end of the robot arm 12 is different from that in a direction perpendicular thereto, so as to thereby indicate for the user 20 that the direction with the soft, i.e. low, modulus of elasticity is the direction in which he or she is to exert the force. Also, if the position of the upper or lower limb of the user 20 is changed in a direction of increasing the output at the distal end of the upper or lower limb, then the modulus of elasticity is changed in its increasing direction. Conversely, if the position of the upper or lower limb of the user 20 is changed in a direction of decreasing the output at the distal end of the upper or lower limb, then the modulus of elasticity is changed in its decreasing direction.

Referring to FIGS. 6 and 7, a vector a, beginning at a hip joint and terminating at a foot joint, and a vector b, beginning at a knee joint and terminating at the foot joint, as the directions in a work space, are taken as base vectors. The direction in which the force is to be exerted, that is, the vector p, is represented by linear combination of the vectors a and b, as expressed by the following expression (1), $$\vec{p}_s = \alpha \vec{a} + \beta \vec{b} \tag{1}$$

If the values of $\alpha$ and $\beta$ are constant, the ratio of the contractile force of the respective function-based muscles of praxis becomes constant.

If the vector perpendicular to the vector p is labeled vector q, then the vector q may be represented by the following expression (2), $$\vec{q}_s // J \begin{pmatrix} \alpha \\ \beta \end{pmatrix} \tag{2}$$

where J denotes the Jacobian determinant at the distal end of the bi-articular arm mechanism Additionally, the following expression (3) is valid, $$KP = K(\vec{p}_s \ \vec{q}_s) = (K\vec{p}_s \ K\vec{q}_s) = p\begin{pmatrix} \lambda_1 & 0 \\ 0 & \lambda_2 \end{pmatrix} \tag{3}$$

Hence, the relationship between the joint torque and the displacement of the distal end of the bi-articular arm mechanism may be represented by the following expression (4), $$K = P\begin{pmatrix} \lambda_1 & 0 \\ 0 & \lambda_2 \end{pmatrix} P^{-1} \tag{4}$$

If the above relationship is rewritten into the relationship between the joint torque and the displacement of the joint angle (stiffness of the joint angle), with the use of the relationship between the displacement of the distal end of the bi-articular arm mechanism and the displacement of the joint angle, then the following expression (5) will be obtained, $$G = \begin{pmatrix} g_{11} & g_{12} \\ g_{21} & g_{22} \end{pmatrix} = J^T P \begin{pmatrix} \lambda_1 & 0 \\ 0 & \lambda_2 \end{pmatrix} P^{-1} J \tag{5}$$

Since J is the Jacobian determinant, the above relationship is the function of the joint angle. Hence, in order to find the elements of the matrix J, actual joint angles are measured by joint angle detection units provided at the joints of the robot arm 12.

If we proceed with transformation of the expression for G, then the following expression (6) will be obtained, $$G = \frac{|\vec{a} \times \vec{b}|^2}{|\vec{p}|^2} \lambda_1 \begin{pmatrix} \beta^2 & -\alpha\beta \\ -\alpha\beta & \alpha^2 \end{pmatrix} + \frac{1}{|\vec{p}|^2} \lambda_2 \begin{pmatrix} (\vec{p} \cdot \vec{a})^2 & (\vec{a} \cdot \vec{p})(\vec{p} \cdot \vec{b}) \\ (\vec{a} \cdot \vec{p})(\vec{p} \cdot \vec{b}) & (\vec{p} \cdot \vec{b})^2 \end{pmatrix} \quad (6)$$

The eigenvalue and the eigenvector of the matrix of the first term of the expression (6) are then calculated. Thus, the following expressions (7) are obtained, $$\lambda = 0, \begin{pmatrix} \alpha \\ \beta \end{pmatrix} \quad (7)$$

$$\lambda = \alpha^2 + \beta^2, \begin{pmatrix} \beta \\ -\alpha \end{pmatrix}$$

where $$\begin{pmatrix} \beta \\ -\alpha \end{pmatrix}$$

is equal to the torque at a joint at the time of exerting the force of the vector p. Specifically, the first term is the response in the τ1-τ2 plane at the time of displacement in the direction of the vector p.

The eigenvalue and the eigenvector of the matrix of the second term of the expression (6) are then calculated. Thus, the following expressions (8) are obtained, $$\lambda = 0, \begin{pmatrix} \vec{p} \cdot \vec{b} \\ -\vec{p} \cdot \vec{a} \end{pmatrix} \quad (8)$$

$$\lambda = (\vec{p} \cdot \vec{a})^2 + (\vec{p} \cdot \vec{b})^2, \begin{pmatrix} \vec{p} \cdot \vec{a} \\ \vec{p} \cdot \vec{b} \end{pmatrix}$$

where $$\begin{pmatrix} \vec{p} \cdot \vec{b} \\ \vec{p} \cdot \vec{a} \end{pmatrix}$$

is equal to the torque at a joint at the time of exerting the force of the vector q. That is, the second term is the response in the τ1-τ2 plane at the time of displacement in the q-direction.

From the above expressions (6) (7) and (8), G may be expressed by the following expression (9), $$G = \lambda_1' \begin{pmatrix} \beta^2 & -\alpha\beta \\ -\alpha\beta & \alpha^2 \end{pmatrix} + \lambda_2' \begin{pmatrix} (\vec{p} \cdot \vec{a})^2 & (\vec{a} \cdot \vec{p})(\vec{p} \cdot \vec{b}) \\ (\vec{a} \cdot \vec{p})(\vec{p} \cdot \vec{b}) & (\vec{p} \cdot \vec{b})^2 \end{pmatrix} \quad (9)$$

If G is expressed as indicated by expression (9), then a large variety of responses may be created in the p and q directions, by fitting various expressions to τ'1 and τ'2. For example, G expressed by the above expression (6) represents a state in which the moduli of elasticity in the directions p and q in a work plane are not changed.

In consideration of changes due to the joint angle and the force direction, between the torque generated by the joint axle and the force generated at the distal end of the link system by the torque generated by the joint axle, if such a relationship is taken that, in the above expression (9), $$\lambda_1' = \frac{((\vec{a} \times \vec{b}) \cdot \vec{z})}{|\vec{p}|} \lambda_1 \quad (10)$$

$$\lambda_2' = \frac{\lambda_2}{|\vec{p}| \sqrt{(\vec{a} \cdot \vec{p})^2 + (\vec{b} \cdot \vec{p})^2}}$$

then the stiffness ellipse is varied responsive to changes in the hexagon of the output at the distal end of the link system.

FIG. 8, portions (a) to (d), show changes in the hexagon 300 and the stiffness ellipse 302 of the output at the distal end in case the direction of the vector p is coincident with the vector a, downward direction in FIG. 8 as indicated by a line segment 304. It may be seen that, as the second joint is stretched, both the hexagon 300 and the stiffness ellipse 302 of the output at the distal end are elongated and contracted in the direction of the vector a, and in the direction perpendicular to the vector a, respectively. The hexagon 300 and the stiffness ellipse 302 are changed in the same manner as above regardless of which direction is actually taken by the direction of the vector p.

Thus, with the present illustrative embodiment, the modulus of elasticity at the distal end of the robot arm 12 may be made anisotropic so as to follow changes, with changes in angle at the first and second joints, of the force that may be exerted at the distal end of the bi-articular link system by the three pairs of muscles of praxis, i.e. six muscles. More specifically, the stiffness characteristics at the distal end of the robot arm 12, fastened to the upper or lower limb of the user 20, may be varied in keeping with positional changes of the upper or lower limb of the user 20. Hence, the modulus of elasticity becomes higher when the upper or lower limb of the user 20 takes a position such as to allow a greater force to be exerted, whereas the modulus of elasticity becomes lower when his or her upper or lower limb takes a position such as to allow only a smaller force to be exerted, respectively. Thus, the direction in which the user 20 proceeding to evaluating or training his or her muscular force is to exert the force may definitely be indicated for the user 20.

An alternative embodiment of the present invention will now be described. In the alternative embodiment, like parts or components are designated with the same reference numerals, and repetitive description there of will be dispensed with. The operation and advantages, which are similar to those of the illustrative embodiment described earlier, will not repetitively be described for simplicity either.

Figure 9:
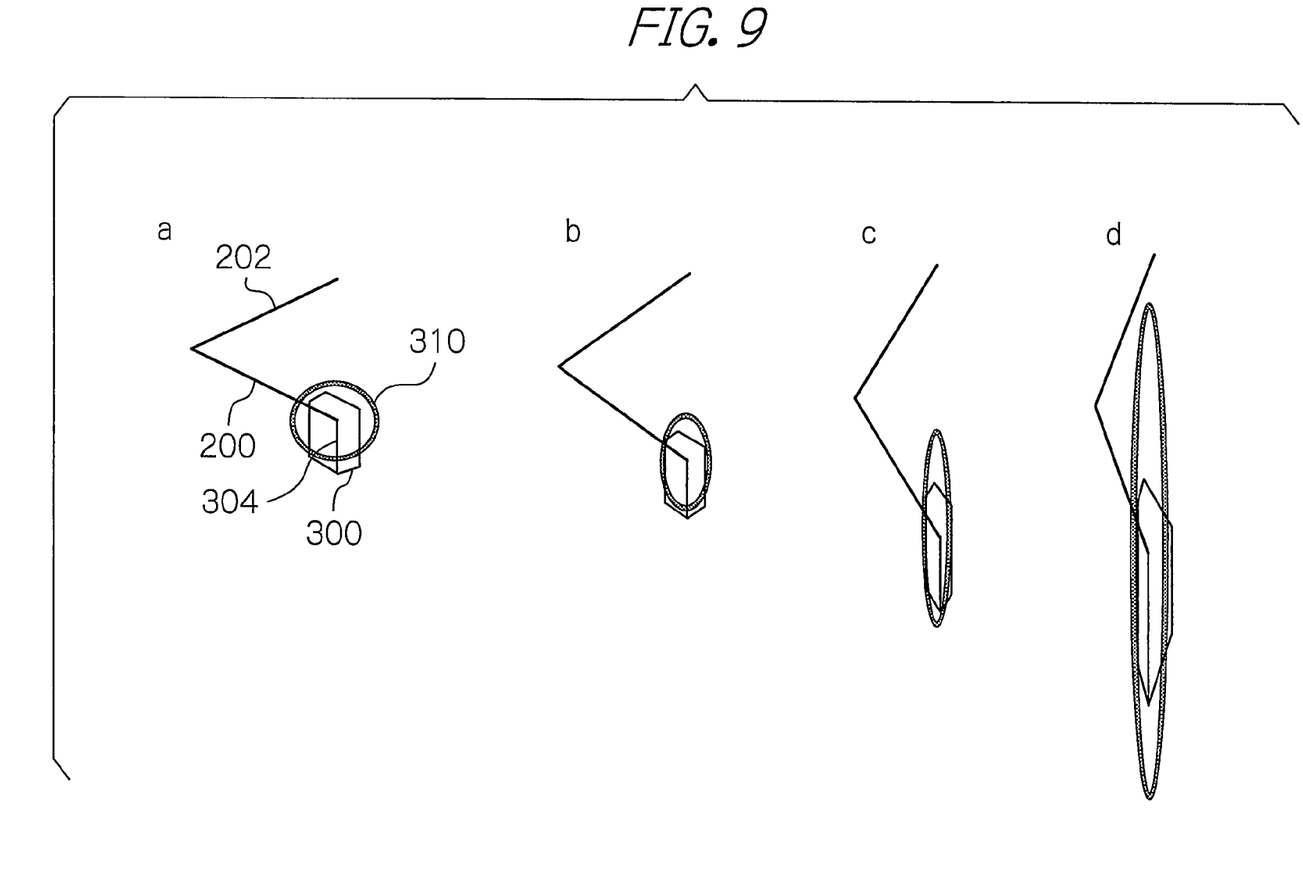
FIG. 9 schematically shows the output distribution according to an alternative embodiment of the present invention.

FIG. 9, portions (a) to (d), show changes in the stiffness ellipse 310 for various stretched states of the second joint in the alternative embodiment. Here, the Eigenvalues of the first and second terms of the above expression (9) are made constant so that the size of the stiffness ellipse 310 in the τ1-τ2 plane will be substantially constant. That is, the scalars of the first and second terms in the above expression (9) are assumed to be represented by the following expression (11), $$\lambda_1' = \frac{\lambda_1}{\alpha^2 + \beta^2} \lambda_1 \quad (11)$$

-continued $$\lambda'_2 = \frac{\lambda_2}{(\vec{p}\cdot\vec{a})^2 + (\vec{p}\cdot\vec{b})^2}$$

The maximum torque is unchanged which may simultaneously be generated by the function-based muscles of praxis at the first and second joints. Hence, by setting the eigenvalue so as to be constant to minimize changes in size of the stiffness ellipse 310 in the τ1-τ2 plane, the stiffness ellipse 310 of the link system in the work plane under goes changes in shape that are close to the hexagonal shape representing the output at the distal end of the link system.

FIG. 9 shows changes in hexagonal output and the stiffness ellipse at the distal end of the link system in case the direction of the vector p is brought in register with the vector a, downwardly directed vector in FIG. 5, in the instant alternative embodiment. It may be seen from FIG. 9, portions (a) to (d) that, although the changes in the stiffness ellipse 310 are greater than those in the output hexagon at the distal end of the link system, both the output hexagon 300 and the stiffness ellipse 310 are elongated in the direction of the vector a, whereas the output hexagon 300 and the stiffness ellipse 310 are contracted in the direction perpendicular to the vector a, as the second joint is stretched. It should be noted that these changes in the output hexagon 300 and the stiffness ellipse 310 remain the same regardless of which direction is actually taken by the direction of the vector p.

In the present alternative embodiment, the scalar G is represented by the above expression (11), whereby the processing load on the controller 19 of the resistance-based muscular force evaluation and training apparatus 10 may be reduced. That is, with the illustrative embodiment described earlier, the scalar G is represented by the expression that follows the changes in hexagonal shape at the distal end of the link system. Hence, square root operation is needed in the course of the processing, thus increasing the processing load on the controller. With the present alternative embodiment, however, processing may be finished more simply by the four arithmetic operations, as the changes in output at the distal end are matched in direction to the changes in the stiffness ellipse. Hence, it is sufficient to use a controller with lower processing capability.

The entire disclosure of Japanese patent application No. 2007-048517 filed on Feb. 28, 2007, including the specification, claims, accompanying drawings and abstract of the disclosure is incorporated herein by reference in its entirety.

While the present invention has been described with reference to the particular illustrative embodiments, it is not to be restricted by the embodiments. It is to be appreciated that those skilled in the art can change or modify the embodiments without departing from the scope and spirit of the present invention.

What is claimed is:

1. A system for resistance-based evaluation and training of a muscular force of a bi-articular link mechanism of a trainee, said system comprising a robot arm which comprises:
   a first link having opposite ends respectively connectable to a first joint and a second joint; and
   a second link having one end connectable to the second joint and another end corresponding to a distal end of the bi-articular link mechanism,
   the bi-articular link mechanism including a set of antagonistic mono-articular muscles about the first joint and another set of antagonistic mono-articular muscles about the second joint, both sets of muscles producing an exercise movement in a plane including the first and second joints and the distal end of the link mechanism, and a set of antagonistic bi-articular muscles astride the first and second joints,
   said robot arm having a distal end secured to the distal end of the link mechanism, the distal end of said robot arm exhibiting elasticity variable with direction;
   the elasticity being variable to follow a change associated with an angular change of the first and second joints in a force exerted at the distal end of the link mechanism by the set of antagonistic mono-articular muscles and the set of antagonistic bi-articular muscles,
   the variable elasticity being used to indicate the trainee of a direction in which he or she is to exert the force at the distal end of the link mechanism.

2. The system in accordance with claim 1, further comprising:
   a saddle for the trainee to sit on;
   a fastener for securing said robot arm to an upper or a lower limb of the trainee;
   a controller for controlling torques at the first joint and second joint on said robot arm; and
   an angular sensor for sensing a joint angle of said robot arm,
   said robot arm being adjustable to a length of the upper limb or the lower limb of the trainee,
   said controller controlling stiffness at the distal end of said robot arm.

3. The system in accordance with claim 2, wherein the stiffness is expressed in a form of ellipse in a plane having two axes corresponding to the torque at the first joint and the torque at the second joint, the ellipse having a constant eigenvalue in each of a first direction in which the trainee is to exert the force and a second direction substantially perpendicular to the first direction.

4. A resistance-based muscular force evaluation and training apparatus comprising:
   a saddle for a trainee to sit on;
   a robot arm adjustable to a length of an upper limb or a lower limb of the trainee and having a distal end exhibiting elasticity variable with direction;
   a fastener for securing said robot arm to the upper limb or the lower limb of the trainee;
   a controller for controlling torques at first and second joints on said robot arm; and
   an angular sensor for sensing a joint angle of said robot arm,
   said controller exercising control to cause the elasticity to vary to follow a change in position of the upper or lower limb of the trainee to use the variable elasticity to indicate the trainee of a direction in which the trainee is to exert a force to measure his or her muscular force.

5. The apparatus in accordance with claim 4, wherein said controller controls stiffness at the distal end of said robot arm, the stiffness being expressed in a form of ellipse in a plane having two axes corresponding to the torque at the first joint and the torque at the second joint, the ellipse having a constant eigenvalue in each of a first direction in which the trainee is to exert the force and a second direction substantially perpendicular to the first direction.

6. A method for resistance-based evaluation and training of a muscular force of a bi-articular link mechanism of a trainee, wherein the bi-articular link mechanism includes a set of antagonistic mono-articular muscles about a first joint and another set of antagonistic mono-articular muscles about a second joint, both sets of muscles producing an exercise movement in a plane including the first and second joints and a distal end of the link mechanism, and a set of antagonistic bi-articular muscles astride said first and second joints, said method comprising:
  preparing a robot arm including a first link having opposite ends respectively connectable to the first joint and second joint, and a second link having one end connectable to the second joint and another end corresponding to the distal end of the link mechanism;
  causing elasticity at a distal end of the robot arm, when secured to the distal end of the link mechanism, to follow a change associated with an angular change of the first and second joints of a force exerted at the distal end of the link mechanism by the set of antagonistic mono-articular muscles and the set of antagonistic bi-articular muscles; and
  using the variable elasticity to indicate a direction in which the trainee is to exert the force at the distal end of the link mechanism.

7. The method in accordance with claim 6, further comprising controlling stiffness at the distal end of the robot arm, the stiffness being expressed in a form of ellipse in a plane having two axes corresponding to the torque at the first joint and the torque at the second joint, the ellipse having a constant eigenvalue in each of a first direction in which the trainee is to exert the force and a second direction substantially perpendicular to the first direction.

* * * * *